(12) United States Patent
Koziollek et al.

(10) Patent No.: US 6,218,172 B1
(45) Date of Patent: Apr. 17, 2001

(54) MICROBIOLOGICAL METHOD FOR ELIMINATING HALOGENATED ETHENES

(75) Inventors: Petra Koziollek, Stuttgart; Dieter Bryniox, Dusslingen; Hans-Joachim Knackmuss, Leonberg, all of (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/284,027

(22) PCT Filed: Oct. 7, 1997

(86) PCT No.: PCT/DE97/02313

§ 371 Date: Apr. 6, 1999

§ 102(e) Date: Apr. 6, 1999

(87) PCT Pub. No.: WO98/15338

PCT Pub. Date: Apr. 16, 1998

(30) Foreign Application Priority Data

Oct. 7, 1996 (DE) ............................................... 196 41 268
Mar. 7, 1997 (DE) ............................................... 197 09 453

(51) Int. Cl.$^7$ ..................................................... C12S 13/00
(52) U.S. Cl. ..................... 435/262.5; 435/266; 210/610
(58) Field of Search ................................ 435/262, 262.5, 435/266, 244, 245; 210/610, 611, 605

(56) References Cited

FOREIGN PATENT DOCUMENTS

| | | |
|---|---|---|
| 40 09 109 A1 | 9/1991 | (DE) . |
| 41 42 063 A1 | 6/1993 | (DE) . |
| 0 336 718 | 11/1989 | (EP) . |
| 0 447 862 | * 9/1991 | (EP) . |

OTHER PUBLICATIONS

Fan et al. "Biodegradation of Trichloroethylene and Toluene by Indigenous Microbial Populations in Soil." Applied and Environmental Microbiology. vol. 59, No. 6 (Jun. 1993), pp. 1911–1918.*

Freedman et al. Caplus Abstract No. 1996:374360 of "The effect of BTEX compounds on aerobic cometabolizm of vinyl chloride by ehtylene grown enrichments." Proc. Water Environment. Fed. Annu. Conf. Expo., 68th (1995), vol. 2, pp. 603–613.*

Gerritse et al. "Complete degradation of tetrachloroethene by combining anaerobic dechlorinating and aerobic methanotropic enrichment cultures." Appl. Microbiol. Biotechnol. vol. 43 (1995), pp. 920–928.*

* cited by examiner

Primary Examiner—William H. Beisner
(74) Attorney, Agent, or Firm—Barnes & Thornburg

(57) ABSTRACT

Process for the microbiological clean up of halogenated ethenes, characterized in that bacterial strains which are growing with ethene as carbon and energy source and break down halogenated ethenes are preadapted with ethene as carbon and energy source for new formation and for energy supply and are contacted in an aerobic bioreactor with the halogenated ethenes to be cleaned up.

13 Claims, 1 Drawing Sheet

MICROBIOLOGICAL METHOD FOR ELIMINATING HALOGENATED ETHENES

CROSS-REFERENCES TO RELATED APPLICATIONS

This application is a U.S. national application of international application serial No. PCT/DE97/02313 filed Oct. 7, 1997, which claims priority to German Serial Nos. 196 41 268.4 and 197 09 453.8 filed Oct. 7, 1996 and Mar. 7, 1997, respectively.

BACKGROUND AND SUMMARY OF THE INVENTION

Halogenated ethenes, in the past, have had widespread use, inter alia, as degreasing agents in the metal processing industry and in textile cleaning. In the interim, these substances which are hazardous to health have become detectable in many places in groundwater and in soil.

Pollution incidents are principally treated by extraction of soil air or by stripping the groundwater aquifer with air. The exhaust air loaded with volatile components is then passed over activated carbon filters. In the course of this the pollutants are removed from the exhaust air stream by adsorption to the activated carbon. The loaded activated carbon can be regenerated and reused for cleaning up the exhaust air streams. If regeneration of the activated carbon is uneconomic, as in the case of the clean up of exhaust air streams with a low level of pollution, the activated carbon is incinerated together with the adsorbed pollutants.

In the incineration of chlorinated-hydrocarbon-loaded activated carbon, polychlorinated dioxins can form. The "17th regulation on the Federal German Air Pollution Control Act" therefore prescribes a dioxin limiting value of 0.1 $ng/m^3$ of exhaust air for the thermal treatment of waste. Regeneration of activated carbon is uneconomic if only low concentrations of the pollutants to be removed are present in the exhaust air stream to be cleaned up and therefore the activated carbon has only a low loading on account of the adsorption isotherms. At low pollutant concentrations in the exhaust air to be cleaned up, on account of the low loading capacity, large amounts of activated carbon are required. The thermal disposal of this activated carbon has a considerable effect on the economic efficiency of the process, as a significant cost factor, in the case of soil and groundwater remediation.

In practice, the exhaust air stream is frequently only cleaned up in the initial phase of remediation using activated carbon filters at high pollutant concentrations. If the pollutant concentration decreases in the course of the remediation process below the statutorily prescribed limiting values of the German Air Pollution Control Regulations, as is usual in the extraction of soil air, the exhaust air is released to the atmosphere without clean up. This redistribution of the pollutants of soil, groundwater and soil air into the atmosphere is questionable for ecological reasons.

Soil, and especially groundwater, are highly protected materials. For reasons of environmental policy, therefore, attempts are made for the permanent remediation of chlorinated hydrocarbon pollutants, without causing a redistribution of the chlorinated hydrocarbons into the atmosphere. The clean up of exhaust air streams having a low level of pollution from the extraction of soil air is highly cost-intensive, however, since large amounts of activated carbon having a low level of pollution are produced which cannot be regenerated economically and must be disposed of thermally with high costs.

Under anaerobic conditions, in the case of pollution incidents caused by tetrachloroethene (PCE) and trichloroethene (TCE), owing to the activity of the autochthonous microflora of the soil, vinyl chloride (VC), which is a particular problem, is formed. Firstly, it is known to be carcinogenic and teratogenic, secondly, it is adsorbed to activated carbon only in extremely low amounts which are not industrially relevant. Chlorinated hydrocarbon pollution incidents having relatively high VC concentrations are therefore not considered to be remediable using the described methods of the current prior art.

For these reasons, biological processes suggest themselves as inexpensive alternative for cleaning up contaminated soil, groundwater and soil air. One possibility is, for example, to inject methane into the soil in order to enrich and activate there methane-oxidizing (methylotrophic) bacteria.

The biodegradation rate is dependent on the number of chlorine substituents and the presence or absence of oxygen. Highly chlorinated hydrocarbons, in particular PCE, are only biodegraded under anaerobic conditions, but lightly chlorinated hydrocarbons, in contrast, are predominantly biodegraded under aerobic conditions. Methane-oxidizing (methylotrophic) and aromatic-degrading bacteria are, for example, able to mineralize TCE, that is to convert it to carbon dioxide, water and chloride. The initial attack is made by an oxygenase. However, the oxygenase reaction forms a highly reactive epoxide which damages and deactivates the cell. The damage is caused by alkylation of cell proteins. The strain Pseudomonas putida F1 is deactivated very rapidly, for example, by the TCE conversion. The oxygenase activity decreases in the course of 20 minutes to 2% of the initial activity.

EP 0 447 862 B1 describes a process for the biological purification of gas streams contaminated with halogenated ethenes and/or halogenated butadienes, in particular from soil air. In this process, expensive growth substrates (auxiliary substrates) such as isoprene and/or butadiene are used. In practice, this process proved to be cost-intensive, since the bacteria used for regeneration must be supplied with relatively large amounts of isoprene. Since isoprene is a relatively readily degradable compound, the risk of an external infection by non-dehalogenating bacteria is very high and can only be prevented by complex sterile techniques which have considerable effects on the operating costs.

EP A 0 336 718 describes a further process for the microbiological degradation of trichloroethene using genetically modified microorganisms. Before using such a process for remediating pollution incidents, particular safety measures must be taken and laborious approval processes are required. Furthermore, problems with public acceptance cannot be excluded.

DE-A 3 326 057 describes a process for the biological clean up of exhaust air. Monochlorinated and dichlorinated alkanes, chlorobenzene and chlorotoluene can be mineralized by the microorganisms used. Degradation of halogenated ethenes is not described.

None of the processes is suitable for degrading PCE.

Starting from this, the object of the present invention is to specify a process for the microbial removal/elimination of halogenated ethenes, with which process a simple and complete degradation is possible.

The object is achieved by the characterizing features of claim 1. The subclaims indicate advantageous developments.

BRIEF DESCRIPTION OF THE DRAWINGS

The FIGURE shows the growth of a bacterial culture preadapted with ethene wherein the bacteria are growth in the presence of ethene. The FIGURE also shows the simultaneous breakdown of cis-1,2-dichloroethene.

DETAILED DESCRIPTION OF THE INVENTION

Figure 1:
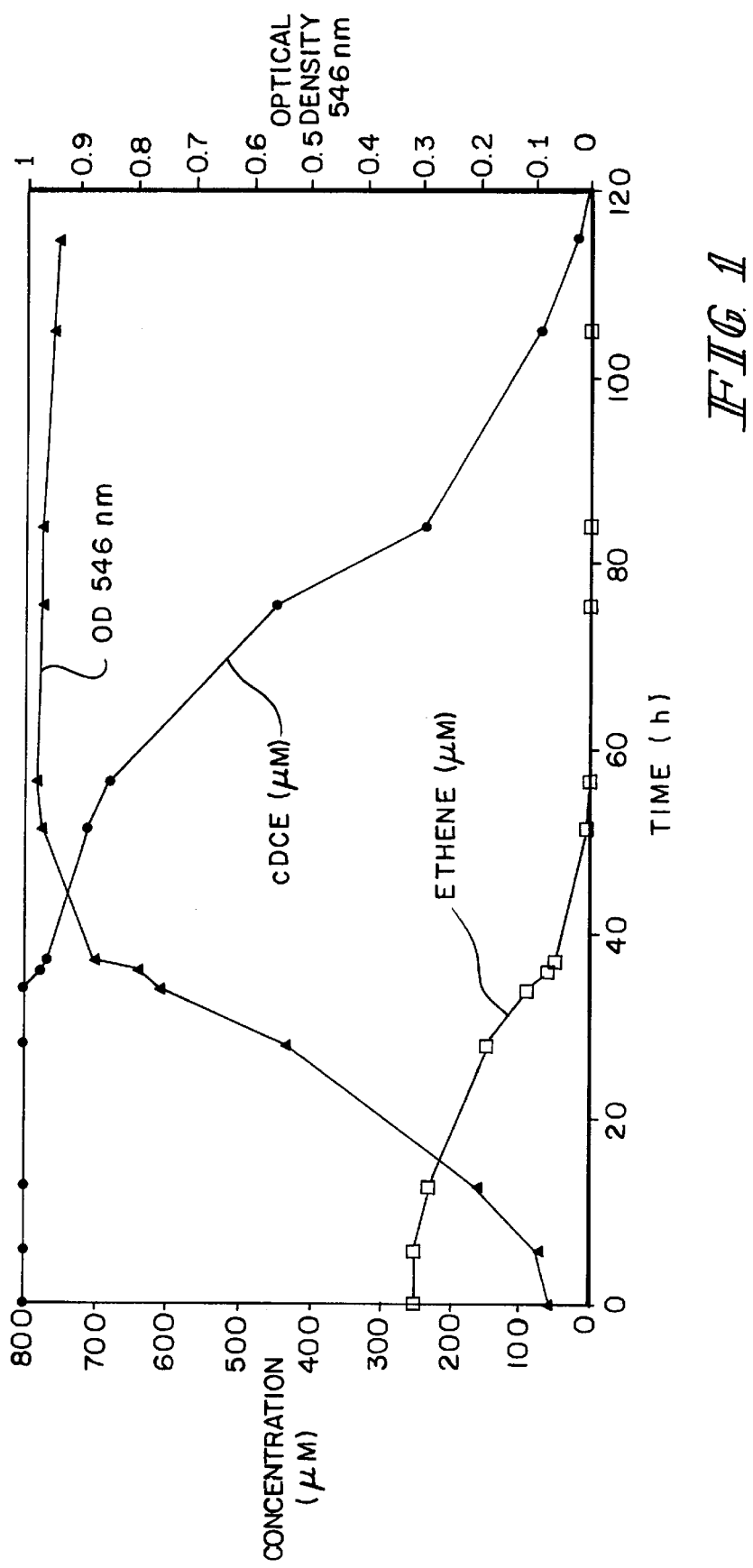

According to the invention it is thus proposed to enrich bacteria which utilize ethene as carbon and energy source which simultaneously are able to mineralize halogenated ethenes as carbon, e.g. cDCE. In a bioreactor, these bacteria are supplied with ethene as carbon and energy source. The halogenated ethenes to be degraded are passed into the bioreactor together with the preadapted microorganisms. There, the chloroethenes are completely mineralized. The auxiliary substrate ethene and halogenated ethenes can be degraded simultaneously. The process is particularly suitable for cis-1,2-dichloroethene and/or vinyl chloride, which can be cleaned up in concentrations of up to 100 mg/l.

Using the process according to the invention it has become possible to clean up groundwater, for example, which is contaminated with all halogenated ethenes, including PCE and VC. This is also possible in the case of groundwater and soil having a low level of pollution.

Preferably, the process according to the invention is carried out in such a manner that it is employed in combination with an anaerobic stage. As the first stage, in this case, use is made of the measure known from the prior art where anaerobic bacteria and mixed cultures are able to dehalogenate chloroethenes reductively. In this case, PCE is converted stepwise, with release of chloride, to TCE, cis-dichloroethene (cDCE), VC and ethene. Since the two first dehalogenation steps proceed highly efficiently and rapidly, but the dehalogenation of CDCE and, in particular, VC proceed at rates which are not relevant industrially, the abovedescribed anaerobic reductive dehalogenation is combined with the process according to the invention.

In addition, using the process according to the invention, it has become possible to clean up in situ not only groundwater contaminated with halogenated ethenes, but also soil and soil air. The in-situ clean up of the contaminated soil can be performed by adding suitable energy and carbon sources, such as molecular oxygen, carbohydrates, alcohols or organic acids, to the groundwater after the treatment in the bioreactor and infiltrating the mixture into the soil. An anaerobic environment is thus created and aerobic, reductively dehalogenating, autochthonous microflora is activated. Owing to a hydraulic circulation, the highly chlorinated ethenes PCE and TCE in the soil are dehalogenated to cDCE. The groundwater is pumped off and treated, for example, above the ground surface in bioreactors. The chloroethenes present in the soil air dissolve in the groundwater treated by clean filtration. Remaining residues of the chlorinated hydrocarbons can be degraded by using the soil air to aerate the aerobic bioreactor.

Surprisingly, it has been found that ethene-degrading bacteria are able to degrade halogenated ethenes. The ethene-degrading bacterial strains described earlier, for example, by Habets-Crüitzen et al. (1984) from the working group of de Bont, achieved degradation rates for ethene of from 9 to 50 nmol/·$mg_{protein}$. Hou et al. (1983) describe an oxidation of ethene by bacteria which had been grown on propane. In this case, from 1.2 to 43 nmol/min·$mg_{protein}$ were measured. Ewers (1991) enriched ethene-degrading bacterial cultures, but made no statements on the degradation rates. He also studied the ethene-degrading cultures for utilization of chloroethenes and chloride release, but could not report positive results. In neither Hou et al. (1983), Heyer (1976) nor the publications from the deBont working group are there indications of degradation of or a chloride release from chlorinated ethenes by ethene-utilizing bacteria.

The bacterial cultures underlying the process according to the invention degrade ethene at rates of up to 60 nmol/min·$mg_{protein}$ and are able to mineralize halogenated ethenes, such as cDCE, completely and thus also to tolerate extremely high concentrations of these toxic compounds. The high resistance to halogenated ethenes is based on the fact that the epoxides primarily formed in the oxidative degradation are very effectively detoxified by the ethene-utilizing bacterial strains.

In the first step of the degradation sequence, ethene is oxidized to ethylene oxide by an oxygenase reaction by the microorganisms which are capable of utilizing this substrate ethene. To prevent cell damage by this highly toxic compound ethylene oxide, which is also used for sterilization purposes, these microorganisms are induced to form a highly efficient epoxide-cleaving enzyme system which detoxifies the ethylene oxide. This enzyme system is also able to cleave the epoxides resulting from chloroethenes in the primary oxidation step. In this manner, preadapted microorganisms can tolerate and dehalogenate even high concentrations of halogenated ethenes.

Suitable bacteria for carrying out the process according to the invention are obtained by enrichment with ethene as sole carbon and energy source according to techniques known to those skilled in the art using samples from suitable locations which have been exposed to both ethene and also chloroethenes. Bacterial cultures which have been enriched in this manner have the following surprising properties:

high tolerance to halogenated ethenes, such as cDCE,
high degradation activity to halogenated ethenes, such as cDCE,
ability to degrade simultaneously halogenated ethenes and the auxiliary substrate ethene,
low requirement for ethene as auxiliary substrate,
low susceptibility to external infection when the process according to the invention is used.

Examples of suitable bacterial strains are PS5 (representative of the α-subgroup of the proteobacteria*), KD20 (Corynebacterium spec. nov.), KL1 (Mycobacterium spec. nov.), KL2 (Mycobacterium spec. nov.), KL3, KL4 representatives of the α-subgroup of the proteobacteria*), KL5 or mixed cultures. * The strains KL4 and PS5 are being determined still more precisely by the Deutsche Sammlung von Mikroorganismen GmbH in Braunschweig.

The chlorinated hydrocarbon degradation by the isoprene- and/or butadiene-degrading bacterial strains described in EP 0 447 862 B1 only takes place in the absence of suitable carbon and energy sources. After some hours of the chlorinated hydrocarbon degradation, their activity decreases owing to the lack of energy which gradually occurs, so that they must be reactivated by adding isoprene and/or butadiene. In contrast thereto, the bacterial cultures underlying the invention are able to break down chloroethene and ethene simultaneously, so that regeneration cycles which are complex in engineering terms are unnecessary. The degradation of chloroethenes, in the case of all bacterial cultures described to date in the specialist and patent literature requires the use of the respective suitable auxiliary substrate in excess. Surprisingly, the ethene-degrading bacterial strains underlying the invention merely require a significantly lower amount of the auxiliary substrate ethene—compared with the halogenated ethenes—to maintain the energy metabolism and the degradation activity with respect to chloroethenes. Therefore, for the process according to the invention, low concentrations of the auxiliary substrate can be used, as a result of which the economic efficiency increases. The microorganisms are supplied with ethene via the gas phase. The concentrations are so low (below 2.3% (v/v)) that no explosive gas mixture can form, as a result of which complex explosion-prevention measures become inapplicable.

Individual enriched bacterial cultures have the capacity, even over relatively long periods, for productive degradation, that is for the utilization of halogenated ethenes, such as cDCE, as sole energy and carbon source.

It has been found that the ethene-degrading bacterial cultures underlying the invention are insensitive to external infection. Airborne microorganisms or external microorganisms from the water which oxidize ethene and/or halogenated ethenes non-specifically form the highly toxic ethylene oxide or epoxides from the halogenated ethenes, which, in the absence of highly efficient epoxide-cleaving enzyme systems, leads to severe cell damage. In the process according to the invention, therefore, complex and cost-intensive sterile techniques to avoid external infection and to maintain the biodegradation process are unnecessary.

A further advantage of the process according to the invention is that ethene is a relatively inexpensive auxiliary substrate.

The process according to the invention is described in more detail below with reference to illustrative embodiments:

EXAMPLE 1
Enrichment of Suitable Microorganisms

For the enrichment of suitable bacteria, activated sludge from the works effluent treatment plant of an ethene- and chlorinated hydrocarbon-producing industry was used as inoculum. Ethene was used as sole carbon and energy source. For the growth of the liquid cultures, the mineral salt solution specified by Dorn et al. (1974) was used. Ethene was added in concentrations between 3% and 20% (in each case v/v in the gas phase). The incubation took place in shaking flasks having baffles and a nominal volume of 100 ml or 500 ml, in which 10% of the nominal volume was mineral medium, at 30° C. on a rotary shaker at 135 rpm. Bacterial growth was determined by measuring the optical density at a wavelength of 546 nm in a photometer (DU 50, Beckmann Instruments Inc., UK). The bacteria were isolated on agar plates (Agar No. 1 Oxoid Ltd, London, UK) using mineral medium. Ethene was added in this case via the gas phase (1.9% v/v).

EXAMPLE 2
Screening for Dehalogenating Microorganisms

The dehalogenation activity of the enriched bacteria was determined via the amount of chloride produced. For this purpose, the chloride test of Weightman et al. (1985) for cells cultured on plates or a test according to Weightman et al. (1985) modified by Ewers (1991) was used. In each case 1 mM cDCE was used in this test. The cultures having a high degradation potential were recognized by the silver precipitate.

The FIGURE shows the growth of a mixed culture on 250 $\mu$M ethene in the presence of 800 $\mu$M cis-1,2-dichloroethene in a batch culture. The concentrations relate to the liquid phase. Growth was performed in shaking flasks having baffles and a nominal volume of 500 ml. The samples to be studied were withdrawn from the gas space of the flask through a septum using a gas-tight syringe. Ethene and cDCE were detected using a gas chromatograph (injector, detector and oven temperature 250° C., 200° C. and 170° C., FID, Plora PLOT U column (25 m×0.53 mm) using He (30 kPa inlet pressure) as carrier gas). The optical density was determined at 546 nm. Cis-1,2-dichloroethene is broken down at the end of the exponential phase and during the stationary phase.

What is claimed is:

1. A microbiological process for removing halogenated ethenes comprising, preadapting a bacterial strain with ethene as a carbon and an energy source wherein said bacterial strain breaks down halogenated ethenes, supplying said bacterial strain with ethene exogenously as the carbon and/or energy source wherein ethene is introduced into an aerobic bioreactor via the gas phase with the feed air in a concentration of below 2.3% (v/v), and contacting said bacterial strain in the aerobic bioreactor with the halogenated ethenes to be cleaned up.

2. The process according to claim 1, wherein the bacterial strain is contacted with ethene and halogenated ethenes simultaneously and/or consecutively in the aerobic bioreactor.

3. The process according to claim 2, wherein the bacterial strains are contacted in the bioreactor with a water to be cleaned up which comprises halogenated ethenes.

4. The process according to claim 3, wherein contaminated groundwater is cleaned up.

5. The process according to claim 2, wherein contaminated groundwater is cleaned up.

6. The process according to claim 1, wherein the bacterial strains are contacted in the bioreactor with a water to be cleaned up which comprises halogenated ethenes.

7. The process according to claim 6, wherein contaminated groundwater is cleaned up.

8. The process according to claim 1, wherein air contaminated with halogenated ethenes is used for introducing gas into the bioreactor.

9. The process according to claim 8, wherein halogenated-ethene-contaminated soil air is used.

10. The process according to claim 1, wherein, prior to the cleaning stage in the aerobic bioreactor, an anaerobic stage for the reductive dehalogenation of the halogenated ethenes is carried out.

11. The process according to claim 1, wherein cis-1,2-dichloroethene-containing and/or vinyl-chloride-containing water and/or air is cleaned up.

12. The process according to claim 11, wherein concentrations of cis-1,2-dichloroethene and/or vinyl chloride up to 100 mg/l are cleaned up.

13. The process according to claim 1, wherein contaminated groundwater is cleaned up.

* * * * *